United States Patent [19]

Parker

[11] Patent Number: 5,132,232

[45] Date of Patent: Jul. 21, 1992

[54] METHOD AND APPARATUS FOR PREPARATION OF LIQUIDS FOR EXAMINATION

[75] Inventor: James E. Parker, Long Beach, Calif.

[73] Assignee: V-Tech, Inc., Pomoma, Calif.

[21] Appl. No.: 72,424

[22] Filed: Jul. 13, 1987

Related U.S. Application Data

[63] Continuation of Ser. No. 760,473, Jul. 30, 1985, abandoned.

[51] Int. Cl.$^5$ ............................ G01N 1/18; G01N 1/28
[52] U.S. Cl. ..................................... 436/177; 436/180;
436/810; 422/100; 422/101; 422/102;
73/863.21; 73/864.02; 128/763; 128/765
[58] Field of Search ................. 422/58, 100, 101, 102;
436/177, 180, 810; 73/863.21, 864.01, 864.02;
128/763, 765

[56] References Cited

U.S. PATENT DOCUMENTS

| | | | |
|---|---|---|---|
| 2,237,213 | 4/1941 | Brown | 73/864.02 |
| 3,430,497 | 3/1969 | Tenczar | 73/864.01 |
| 3,560,162 | 2/1971 | Mittleman | 436/69 |
| 4,022,576 | 5/1977 | Parker | 436/177 |
| 4,235,725 | 11/1980 | Semersky | 210/927 |
| 4,268,270 | 5/1981 | Gabbay et al. | 422/58 |
| 4,528,187 | 2/1985 | Trugho | 422/102 |
| 4,563,332 | 1/1986 | Mitchell et al. | 422/100 |
| 4,572,210 | 2/1986 | McKinnon | 128/765 |

Primary Examiner—Lynn Kummert
Attorney, Agent, or Firm—Drucker & Sommers

[57] ABSTRACT

Method and Apparatus for collecting liquid analytical samples for examination, particularly whole urine and blood samples, and reproducibly separating them into two or more fractions. A sample is disposed within such an apparatus, then staining with dye or reacting with reagent as necessary without dislodging or disturbing the sample within the apparatus, or the arrangement of the apparatus itself. A sample can be transferred from the apparatus which serves as a preparation zone, to a separate analysis zone. An apparatus is shown of a type utilizing a container and a petter, said petter provided with an upper portion which enables attachment to the container, a lower retainer portion including a peripheral aperture, the non-apertured portion of which enables wedge-fit thereof into the container, and a body portion connecting the upper petter portion and lower retainer portion.

25 Claims, 2 Drawing Sheets

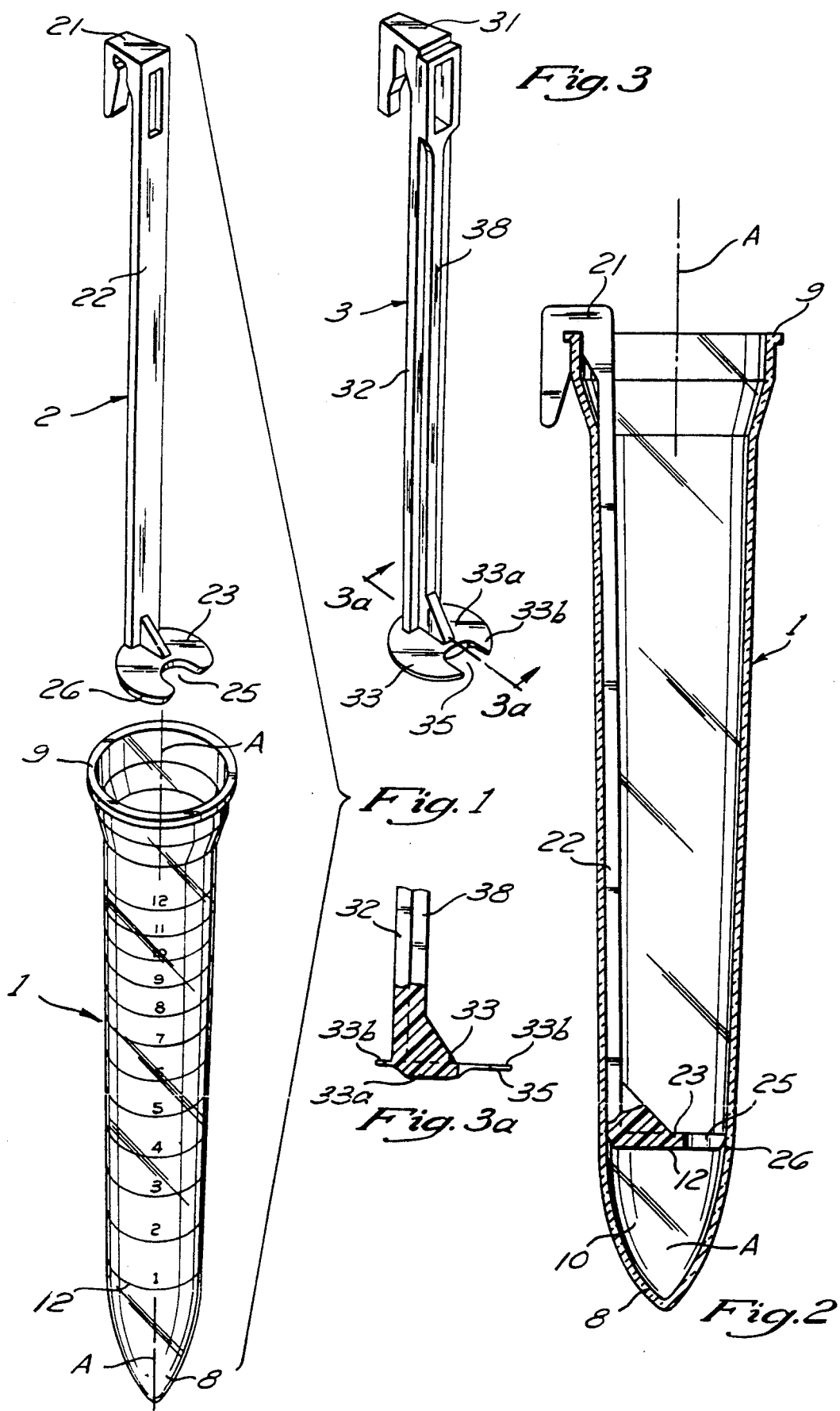

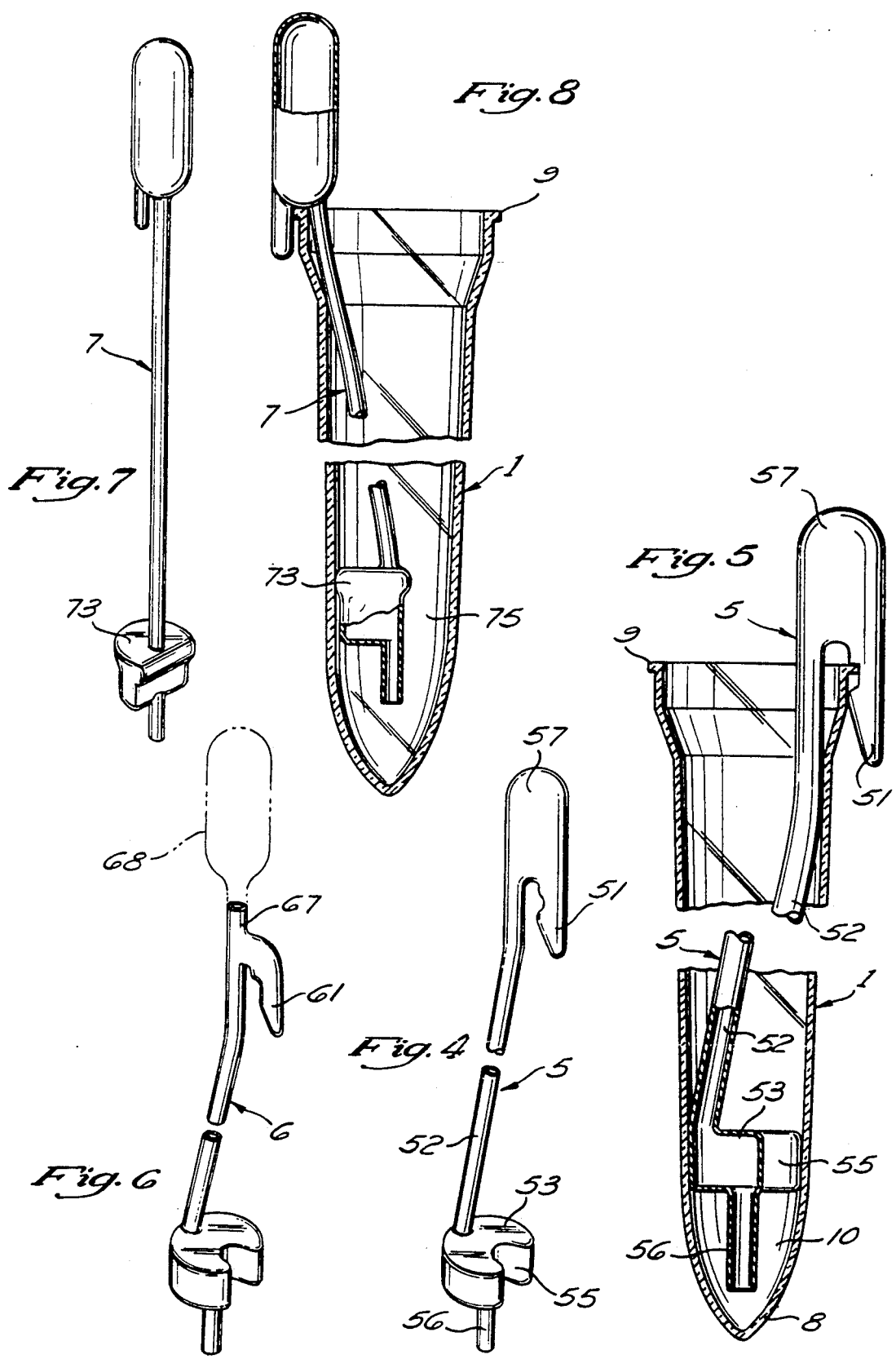

METHOD AND APPARATUS FOR PREPARATION OF LIQUIDS FOR EXAMINATION

This application is a division of application Ser. No. 760,473 filed Jul. 30, 1985, now abandoned.

BACKGROUND OF THE INVENTION

1. Field of the Invention

The necessity and desirability of separating liquid samples such as urine or blood into their respective component parts for examination purposes has long been recognized. It is well known that such a separation can be effected by centrifugation whereby sediments, etc., suspended in the fluid are forced to the bottom of a centrifuge container or test tube, thereby displacing the less dense components to higher levels. In those operations requiring only the sediments (e.g., red blood cell analysis from whole blood, or examination of organized urinary sediments consisting of erythrocytes, leukocytes, epithelial cells, bacteria and casts, as well as unorganized granular or crystalline sediments and the like), typically the supernatant portion is removed and the sediment is resuspended, stained, or otherwise prepared for analysis.

The need for standardized and reproducible techniques for sample preparation and examination is well established. The initial sample volume and the sediment sample volume must be controlled, as well as operator techniques overall and especially in the removal of the supernatant fluid after centrifugation, so that the sediments are conserved and the results are accurate and reproducible. The same requirements obtain for the separation of liquid phase systems.

2. Prior Art

Several past efforts to fill this need have generally provided means for placing a physical barrier into a test tube containing a sample between the sediment and the supernatant before or after the centrifugation. The barrier would typically be designed to remain in place while the supernatant is decanted, aspirated or otherwise poured off. Subsequently, the physical barrier would need to be removed to provide access to the sediment remaining in the test tube for purposes of resuspension, introduction of stain, or removal for examination.

The Parker patent (U.S. Pat. No. 4,022,576) illustrates such a device to be inserted after centrifugation. It provides an insert member which is hollow, closed at its upper end and open at the end to be inserted into the tube. The insert member is further provided with a bead of appropriate size which wedges into a test tube at a point of reduced cross section, and provides a fluid-tight physical barrier at a predetermined distance from the bottom of the tube. The liquids above this barrier are decanted, and then the insert member is removed to allow for the addition of stain to the fraction remaining in the tube, or alternatively, some of the sediment sample remaining in the bottom portion of the test tube may be withdrawn into the hollow insert member, and subsequently the entire insert member is removed from the tube in order to transport the sample contained therein.

The Parker patent has several disadvantages. The primary problem is that proper placement of the insert member in the test tube requires it to be wedged therein, thus it introduces elements of inaccuracy and nonreproducibility, since the firmness of the operator's wedging technique can vary the volume trapped in the test tube below the wedge and thus improperly concentrate or dilute the sediment. Further, due to the sealing engagement provided by the wedge, the insert member must be forcibly released from the test tube; this step is time-consuming and requires pressure to be exerted on the insert member, which increases the risk of losing some of the sample which has been drawn up into the insert member for transfer. Additional time and efficiency is wasted if the sample is to be stained for examination while remaining in the tube, because the insert member must first be entirely removed to provide an opening for the introduction of the stain, and then subsequently reintroduced to transfer the sample elsewhere from the test tube.

An alternative approach to this problem is shown in R. K. Bernstein et al., (U.S. Pat. No. 3,481,712) which utilizes a system which confines the sediments in a liquid sample to the bottom of a centrifuge tube without providing a physical barrier between the supernatant and the sediment phases. This system utilizes a reservoir at the lower end of the centrifuge tube of relatively reduced cross section, further especially adapted to retain a predetermined volume within by the means of surface tension and atmospheric pressure.

While it is advantageous to be thus free from the necessity of removing any insert means to stain or remove the sediment, the lack of any physical restraining means causes a problem at certain standard experimental volumes. Using accepted and standard procedures well known in the art, generally about 10–15 ml of a liquid sample are centrifuged for about five minutes at $400 \times$ g (i.e., 400 times the gravitational acceleration force). (See, e.g. Parker, Bernštein). The solids contained in the liquid, a urine specimen for example, are thereby normally concentrated in the lower 1 ml portion of a centrifuge tube. A preferred embodiment of the Bernstein invention (col. 3, lines 62–75), in contrast, operates at smaller volumes, utilizing 4.1 ml of whole sample and obtaining 0.15 ml of sediment.

In order to obtain the larger standard 1 ml amounts of sediment typically required for analytical purposes, more of a whole sample would be needed, necessitating a larger container and also an enlargement of the sediment reservoir (perhaps by two-thirds) compared to the preferred embodiment. However this would be disadvantageous, as increasing the reservoir in depth or in its cross section would change the surface tension in the apparatus which governs the sediment collection, and thus render experimental results less readily reproducible.

There has long been a need in the field of laboratory analysis for a method and apparatus for accurate, reproducible preparation of liquid-phase specimens and the like, for further chemical and microscopic analysis, which method and apparatus further provides access to two liquid phases without requiring time-consuming and inefficient disruption of the apparatus.

The present invention provides such an enhanced method and apparatus for sample preparation to achieve accurate and reproducible microscopic or chemical examination.

SUMMARY OF THE INVENTION

The present invention resides in an improved method and apparatus for the preparation for examination of small volumes of liquid samples. By use of this invention, the manual collection of a predetermined and readily reproducible volume of liquid sample is achieved in a more reliable, efficient and rapid manner than heretofore.

The apparatus of the present invention comprises, in combination, various components. The first component is an elongated, generally tubular, container open at its normally upper end, and closed at the opposite end, and is referred to herein as the test tube. Preferably, the closed end of said test tube is tapered or cone-shaped to facilitate the collection of suspended solids during centrifugation or the like.

The second component comprises an insertable retaining means, referred to herein as the petter means, or petter. This petter means has an upper end shaped generally like an inverted U, adapted to snap fit onto the upper edge of the test tube, an elongated body portion, and a lower retainer member. The retainer member is shaped generally like a disc with an aperture disposed along its periphery. When the petter means is placed in the test tube, the periphery of said disc is in contact with the inside walls of the test tube, and provides a partial sealing engagement of said petter means with the inner wall of said test tube.

This petter, when securely fastened to the test tube, is precisely located to provide a predetermined, reproducibly accurate volume below the retainer disc. The new petter remains in place once attached to the test tube while removing the liquid fraction located between the retainer member and the open upper end of the test tube, and also provides access through the aperture for introducing a stain to the liquid sample below the retaining disc, or for removing a portion of said liquid sample without disturbing or separating the components of this invention.

It appears that the adaptation of the upper end of the petter means for precisely locating the petter in a container is unknown in the art. Such an upper end may be used with lower retainer members of different configurations, with or without apertured peripheries, without departing from the spirit of this invention. Likewise, a lower retainer member provided with an aperture along its periphery to space said lower retainer member from the inner wall of a container after insertion into such a container appears to be novel, and may be used with or without utilizing an upper petter end adapted to engage the open end of the container, without departing from the spirit of this invention.

In one embodiment, this insertable petter means is generally structured as described above, and is integrally formed, without tubular construction. In another embodiment, the insertable petter is generally structured as described above, but may be of hollow, tubular construction and also sealed at both ends.

In a third embodiment, the petter is provided with hollow, generally tubular, components) the disc-shaped retainer member is provided with an aperture, as described above, and additionally is provided with a generally tubular member projecting downward from the retainer disc into the lower end of the test tube. This petter also is provided with a compressibly-resilient portion proximate to the snap-on upper end, operable to draw a sample through the hollow petter from the fluid at the bottom of the test tube.

In a fourth embodiment, the petter is provided with the same hollow, tubular components of the third embodiment; the disc-shaped retainer member is provided with the aperture and the generally tubular downwardly-projecting member is also provided, as described in the third embodiment. In this fourth embodiment, the snap-on upper end of the petter is adapted to interfit with a separate aspirator means to permit withdrawal of a sample of the fluid at the bottom of the test tube through the tubular, hollow petter.

In all embodiments, the test tubes and the petters are fabricated of relatively inexpensive moldable plastic material.

An example of the method of this invention involves obtaining, by conventional means, a liquid sample containing solid material suspended therein (e.g., a urine or blood sample), inserting said liquid sample into a test tube and then centrifuging same within conventional parameters so that the suspended material lies in the lower end of the test tube.

Next, an insertable petter means of this invention is placed into the test tube so that the petter's upper end lockably engages the rim of the test tube at its upper open end; the petter thereby extends down into the test tube and the periphery of the petter's disc-shaped lower retainer member contacts, at the non-apertured part thereof, the walls of said test tube at a predetermined distance from the lower, closed end of the test tube.

Subsequently, the liquid in the test tube above the retainer member is aspirated, decanted or otherwise removed. The liquid sample below the retainer member, however, does not leak through the aperture because, it is believed, of a combination of surface tension and atmospheric pressure on the liquid sample. The liquid remaining below the retainer member is thereby conserved, in its original volume, and thus an accurate, readily-reproducible liquid sample volume is obtained.

Because of the aperture, the petter may remain in place if a stain or other reagent is introduced to the liquid sample remaining below said retainer (through the aperture in the disc-shaped retainer member).

A separate pipette transfer means may also be inserted into said test tube, through the aperture in the retainer member, to remove some of the liquid remaining in the test tube, if desired. Alternatively, if the inserted petter means is adapted for aspiration of said conserved liquid, as with the third and fourth embodiment, a sample of said conserved liquid may be withdrawn through said petter for microscopic or other analysis of the solids or liquids contained therein.

Although the invention is described herein in connection with urinalysis, it will be appreciated that the invention is not so limited, and finds application in other procedures, for example, blood analysis, liquid-liquid phase and emulsion studies. The present invention is applicable wherever accurate and reproducible analysis of liquids, or liquids containing suspended materials therein, is necessary.

Other aspects and advantages of the present invention will become apparent from the following more detailed description, taken in conjunction with the accompanying drawings.

DESCRIPTION OF THE DRAWINGS

FIG. 1 is an exploded perspective view of a petter and container embodying the features of the present invention.

FIG. 2 is a longitudinal sectional view of the petter and container in assembled position.

FIG. 3 is a perspective view of an alternate form of the petter.

FIG. 3a is a fragmentary sectional view taken along line 3a–3a of FIG. 3.

FIG. 4 is a partly fragmentary perspective view of an alternative form of the petter.

FIG. 5 is a partly fragmentary, elevational, partly sectional view of the container of FIG. 1 and the petter of FIG. 4 in assembled position.

FIG. 6 is a partly fragmentary, perspective view of an alternate form of the petter.

FIG. 7 is a perspective view of an alternate form of the petter.

FIG. 8 is a partly fragmentary, elevational, partly sectional view of the container of FIG. 1 and the petter of FIG. 7 in assembled position.

DETAILED DESCRIPTION OF THE INVENTION

This invention is directed to an improved method and apparatus for the preparation of experimental samples derived from whole (unconcentrated and unfractionated) liquid specimens. This invention readily finds application to the preparation for examination of liquid specimens containing suspended materials and solids therein, as is frequently desired with urinalysis or blood analysis.

Referring to the drawings, it may be seen that this invention comprises various components. The first component, seen in FIG. 1, is a generally cylindrical but tapered container, open at its normally upper end 9 and closed at the opposite end 8, and is referred to herein as the test tube 1.

Preferably, said upper end 9 is outwardly and upwardly funnel-shaped for ease in operator handling, and said closed end 8 is tapered or cone-shaped to facilitate the collection of suspended solids during centrifugation. Additionally, the interior of the tube 1 within its lower end portion is of reduced cross section with respect to the interior cross section adjacent the open end 9. As will be more fully explained hereinafter, a point 12 at a predetermined distance along the longitudinal axis from the closed end 8 is selected such that the lower end portion of the container between the selected point and the closed end will contain a predetermined volume of liquid. This point is referred to herein as the point of contact.

A suitable stopper or cap (not shown) can be provided to seal the open end 9 of the tube 1 during centrifuging, storage, or the like. The test tube 1 may be provided with indicia (shown in FIG. 1) for accurately reflecting the volume of its contents.

A second component 2, seen in FIG. 1, comprises an insertable retainer means, referred to herein as the petter means 2, or petter 2. This petter 2 has an upper end 21, shaped generally like an inverted U, adapted to snap-fit onto the upper edge 9 of the test tube 1, an elongated body portion 22, and a lower horizontally extending retainer member 23. Said upper petter end 21 is adapted to tightly engage the rim 9 of the test tube 1 so as to grip and remain securely in place during any rotation or inversion or other movement of said test tube.

As can be seen in FIG. 1, lower retainer member 23 is shaped generally like a disc with an aperture 25 formed therein. The periphery 26 of member 23 contacts the inner wall of test tube 1, but does not form a fluid-tight seal with the inner wall of test tube 1 due to the presence of the aperture 25. An annular flanged slightly funnel-shaped shoulder may be provided on or proximate to the periphery of member 23 or the periphery 26 might be slightly tapered in an upward or downward direction, as seen in FIG. 2, to enhance the seal at the points of contact between member 23 and the inner wall of tube 1.

The outer circumference of member 23 is selected to permit sufficient clearance between it and the inner wall of tube 1 so that petter 2 is readily insertable through the open end 9 of tube 1, and can pass freely through the tube until further movement is prevented by the engaging of the U-shaped upper end 21 of the petter 2 with the upper edge of tube 1, and as such engagement occurs, the outer periphery 26 of member 23 comes into contact with the inner wall of tube 1 at the point 12, which is the point of contact described above.

An important feature of the present invention is that the member 23, when in contact with the wall of tube 1, be spaced from the closed end 8 of the tube 1 so that a uniform, predetermined volume of liquid is contained in the space beneath the member 23. To this end, the diameter of member 23 is selected to correspond substantially to the internal diameter of tube 1 at the point of contact. An internal annular shoulder or bead of appropriate size (not shown) may be provided in tube 1 to insure a seal at contact points between member 23 and the inner wall of tube 1.

The internal diameter of tube 1 gradually decreases towards its closed end 8, so that a number of points of contact, selected along the longitudinal axis A—A of tube 1, can be utilized with members 23 having different diameters, to form volumes of different sizes.

Petter 2 further has an elongated body portion 22 which connects lower retainer member 23 and upper end 21.

The petter 2, when securely fastened to the test tube 1, is precisely located to provide a predetermined, reproducible, and accurate volume 10 below the retainer member 23 hereinafter sometimes referred to as the "critical volume". Different critical volumes may be formed by utilizing different lengths for the body portion 22, in conjunction with varying the diameter of member 23. Thus, it will be appreciated that the diameter of member 23 varies in direct, inverse relation to the length of member 22.

Petter 2 is preferably integrally molded of any one of a number of relatively inexpensive plastic material such as polyethylene, polypropylene, or polystyrene, and is constructed either, in solid form, as shown in FIGS. 2 and 3, or in tubular form, as is shown in FIGS. 4–8 and as will be described.

An alternative petter 3, which is the presently-preferred embodiment is shown in FIGS. 3 and 3a, wherein it may be seen that the lower retainer member 33 comprises a central inflexible support portion, 33a with a surrounding integrally formed flexible flange or flexible sealing gasket 33b. This flexible flange or gasket 33b advantageously enhances resealing engagement between said lower retainer member 33 and the inner wall of tube 1. In this FIG. 3 embodiment elongated body portion 32 is provided with an elongated support rib 38.

Petter 2 has been shown and described as being of solid, non-tubular construction, but may also be blow-molded in tubular form.

The method for utilizing these embodiments is generally as follows. A liquid containing suspended material therein (e.g., a urine or blood sample) is placed within tube 1 and then centrifuged in a conventional manner at a speed and for a length of time sufficient to locate the previously suspended material in the lower end of tube 1.

An insertable petter means (2, 3) is subsequently placed into said tube 1, so that upper petter end (21, 31) engages the rim of tube 1 at its upper open end 9. The upper petter end (21, 31) reaches the point of engagement denoted by an audible click or snap-like sound, and the petter (2, 3) cannot be further lowered into tube 1.

Thus, elongated body portion (22, 32) extends down into tube 1, and lower retainer member (23, 33) engages the inner wall of tube 1 at a predetermined distance from the closed, lower end 8 of tube 1, as shown in FIG. 2.

Next, the liquid in tube 1 located between lower retainer member (23, 33) and the open end 9 of tube 1 is aspirated, decanted in one quick motion, or otherwise removed by conventional means. The liquid sample located in the critical volume 10 between retainer member (23, 33) and closed end 8 of tube 1 remains therein and does not leak through aperture (25, 35) because of a combination of surface tension and the atmospheric pressure on the liquid sample, it is believed.

While petter (2, 3) remains in place, an amount of stain or dye or another substance may be added to the conserved material through aperture (25, 35). All or a portion of the sample remaining in tube 1 may now be removed by a separate pipette or other transfer means and located elsewhere for analysis or stoppered and stored.

As seen in another embodiment in FIG. 4, a petter 5 is provided with the same general structure as FIGS. 1-3a but is comprised of hollow, tubular components. Lower Retainer member 53 is thicker than comparable retainer members (23, 33) and is provided with aperture 55 as seen in FIG. 4. Aperture 55 may be of generally semi-circular shape as shown or of another suitable configuration. Additionally, petter 5 is provided with a generally tubular member 56 which, when the components of the apparatus are assembled, downwardly projects from retaining member 53 into critical volume 10 toward closed end 8 of tube 1, as seen in FIG. 5. Petter 5 is also provided with a compressibly-resilient bulb portion 57 proximate to upper snap-on end 51, operable through compression and release of pressure on the bulb to form a vacuum sufficient to draw the liquid sample from critical volume 10 up through tubular member 56, retaining member 53 and elongated body portion 52 so that such liquid sample may be transferred therein from tube 1 to an analysis or storage zone.

FIG. 6 depicts another embodiment, wherein petter 6 is provided with the same general structure and hollow tubular components as petter 5. In this embodiment, the snap-on upper end 61 of petter 6 is provided with stem means 67 to interfit with a separate aspirator bulb means 68 (shown by broken lines) to permit withdrawal of a sample from the critical volume 10, as generally described with the petter 5.

FIG. 7 shows petter 7 is provided with the same general structure and hollow tubular components as petter 5. As shown in FIG. 8, lower retainer member 73 is shaped so as to provide a slightly enlarged aperture 75 between the retainer member 73 and the inner wall of tube 1, as compared with, e.g., aperture (55, 35).

These embodiments are provided for illustrative purposes and do not limit the invention to the particular configurations set forth in the figures. It is believed that the adaptation of the upper end of the petter means for precisely locating the petter in a container is unknown in the art. Such an upper end may be used with lower retainer members of different configurations, with or without apertured peripheries, without departing from the spirit of this invention. Likewise, a lower retainer member provided with an aperture along, or within, its periphery to space said lower retainer member from the inner wall of a container after insertion into such a container is believed to be novel, and may be used with or without utilizing an upper petter end adapted to engage the upper end of the container, without departing from the spirit of this invention.

In these and all embodiments, the apparatus may be fabricated by conventional methods and with relatively inexpensive moldable plastic materials such as polyethylene, polypropylene, or polystyrene, and thus are particularly suited as single-use disposable items.

The method of operation for all embodiments is similar in that the petters 2, 3, 5, 6, and 7 need not be removed for addition of stain, dye, etc. and provide an accurate, readily reproducible sample volume.

Although specific embodiments of the invention have been described in detail for purposes of illustration, various modifications may be made without departing from the spirit and scope of the invention. Accordingly, the invention is not to be limited except by the appended claims.

I claim:

1. A petter means for preparing a reproducible small volume of a liquid sample, adapted for use in a container having a closed lower end, and an inner wall extending from the lower end forming a generally increasing cross section, and terminating in an open upper engageable edge, and is usable to define a chamber of readily reproducible and predetermined volume between a location on the inner wall and the closed lower end through engagement with the inner wall cross section, the petter means comprising:
   (a) an upper portion;
   (b) a lower retainer member including a central inflexible support portion and an integrally formed sealing gasket and defining a single aperture therein, said lower retainer member adapted and arranged to engage an inner wall cross section, said lower retainer member occupying a substantial portion of the inner wall cross section engaged by said lower retainer member, said aperture occupying the remaining area, said aperture being of sufficiently small size to prevent leakage, of a liquid sample, and of a sufficiently large size to permit access to a liquid sample by a pipette for addition of substances and for removal of substances; and
   (c) an elongated body portion, connecting said upper portion and said lower retainer member.

2. The petter of claim 1 wherein said upper portion is adapted and arranged to engage an open upper edge.

3. A petter means as in claim 2, wherein the upper end of said petter is shaped generally as inverted U, and is adapted to snap-fit over an open upper edge.

4. A petter means as in claim 1, where the integrally formed sealing gasket is provided with a tapering periphery.

5. A petter means as in claim 1, wherein said petter means is made of a moldable plastic material.

6. A petter means as in claim 5, wherein said petter means is molded as an integral unit.

7. A petter means as in claim 6, wherein said petter means is of solid, non-tubular, construction.

8. A petter means as in claim 6, wherein said petter means is of generally hollow, tubular construction and is also sealed at both ends.

9. A petter means as in claim 1, wherein said petter means is formed of generally hollow components, lying in fluid communication.

10. A petter means as in claim 9, wherein said petter means is provided with a generally tubular member projecting downwardly from said lower retainer member, and which tubular member is open at its lower end.

11. A petter means as in claim 10, wherein said petter means is provided with a compressibly-resilient portion proximate to said upper end, operable through compression and release of pressure to form a vacuum sufficient to withdraw fluid through said petter.

12. A petter means as in claim 10, having a separate aspirations means adapted to interfit with said upper end of said petter means for withdrawal of fluid through said petter.

13. A petter means as in claim 10, wherein said petter is made of a moldable plastic material.

14. A petter means as in claim 10, wherein said petter is molded as an integral unit.

15. A method for the preparation of a liquid sample of reproducible, small volume, for examination and analysis, for use in an apparatus comprising a container which has a closed lower end, an upper open end, and an inner wall, and is of generally decreasing cross section from said open end toward said closed end, and a petter means, removably insertable into said container, usable to define a chamber of readily reproducible and predetermined volume at the lower end of said container through the partial sealing engagement of said petter means and the inner wall of said container, said petter means having an upper end adapted to snap-fit over the upper, open end of said container, and a lower retainer member provided with an aperture therein and an elongated body portion connecting said upper end and lower retainer member, said method comprising the steps of:
(a) placing in said container a liquid of greater volume than that desired for the sample volume,
(b) inserting said petter means into said container so that said upper petter end engages the upper open end of said container whereby said petter means cannot be further lowered into said container, thus precisely locating said lower retainer member at a point of contact between the periphery of said retainer member the inner wall of said container to define a chamber of critical volume, and
(c) withdrawing the excess liquid between the upper open end of said container and said lower retainer member without altering the critical volume located between said lower retainer member and said closed lower end of said container.

16. A method as set forth in claim 15, wherein said liquid contains suspended material therein for preparation of a small, reproducible sample volume for examination and analysis of said suspended material, and further including the step of centrifuging said liquid in said container to locate said suspended material in the closed lower end portion of the container.

17. The method as defined in claim 16, wherein said liquid containing suspended material therein is urine.

18. The method as defined in claim 16, wherein said liquid containing suspended material therein is blood.

19. A method as set forth in claim 15, and further including the step of introducing a reagent such as a stain to said critical volume in the closed lower end portion of said container through a means communicating through said aperture with the closed lower end portion.

20. A method as set forth in claim 15, and further including the step of removing a sample of said conserved liquid through means communicating through said aperture with the closed lower end portion of said container.

21. A method as set forth in claim 15, wherein all components of said petter means are generally hollow, tubular components adapted to lie in fluid communication, and said petter means is further provided with a generally tubular member projecting downwardly from said lower retainer member, and which tubular member is open at its lower end, said petter means being further provided with means for drawing liquid from the lower end of said container into said hollow petter, and further including the step of withdrawing a sample of the conserved liquid located at the closed lower end of said container into the hollow components of said petter.

22. A method as set forth in claim 21, wherein said petter means is provided with a compressibly-resilient portion proximate to said upper end, operable through compression and release of pressure to form a vacuum sufficient to withdraw fluid into said petter, and said step of withdrawing into said hollow petter some liquid from the closed lower end of container includes withdrawing said liquid by compressing and releasing said compressibly resilient portion.

23. A method as in claim 21, wherein the upper end of said petter means is adapted to interfit with separate aspiration means for withdrawal of fluid through said petter, and said step of withdrawing into said hollow petter a sample of the liquid from the closed lower end of said container end includes operation of said separate aspiration means.

24. A method as in claim 15 wherein the step of withdrawing said excess liquid is performed by decantation.

25. A method as in claim 15 wherein the step of withdrawing said excess liquid is performed by aspiration.

* * * * *